United States Patent [19]

Jampel et al.

[11] Patent Number: 4,747,404
[45] Date of Patent: May 31, 1988

[54] FOLDABLE INTRAOCULAR LENS INSERTER

[75] Inventors: Robert S. Jampel, Bloomfield Hills; Dian X. Shi, Detroit, both of Mich.

[73] Assignee: Kresge Eye Institute of Wayne State University, Detroit, Mich.

[21] Appl. No.: 929,008

[22] Filed: Nov. 10, 1986

[51] Int. Cl.$^4$ ............... A61B 17/00; A61B 17/28; A61F 2/16

[52] U.S. Cl. .................. 128/303 R; 128/321; 623/6

[58] Field of Search ............... 128/303 R, 321; 623/6

[56] References Cited

U.S. PATENT DOCUMENTS 4,573,998 3/1986 Mazzocco .................. 623/6

Primary Examiner—C. Fred Rosenbaum
Assistant Examiner—Gene B. Kartchner
Attorney, Agent, or Firm—Cullen, Sloman, Cantor, Grauer, Scott and Rutherford, P.C.

[57] ABSTRACT

A surgical tool for folding and inserting a folded lens into the anterior chamber of an eye through a small incision in the limbus of the eye includes an elongated tube which is longitudinally split into a U-shaped base section and a manually, axially slidable U-shaped cover section. The tube has an elongated, inner portion, which is inserted into the anterior chamber of the eye, and an outer portion. A tubular guide sleeve encircles the outer portion of the base section. A cylindrically-shaped plug is positioned within the base section and sleeve to provide an arcuate space between the plug and the inner wall of the sleeve. The cover section is slidably inserted within the space for guiding and positioning the cover section for overlapping or uncovering the inner end portion of the base section. Means are provided for folding and pressing a lens into the base and holding it there until the cover section is manually slid over the base to encircle the lens within the tube inner portion. When the tube inner portion is arranged within the anterior chamber, the cover section is manually moved axially to uncover the inner portion of the base section which releases the lens within the chamber.

10 Claims, 2 Drawing Sheets

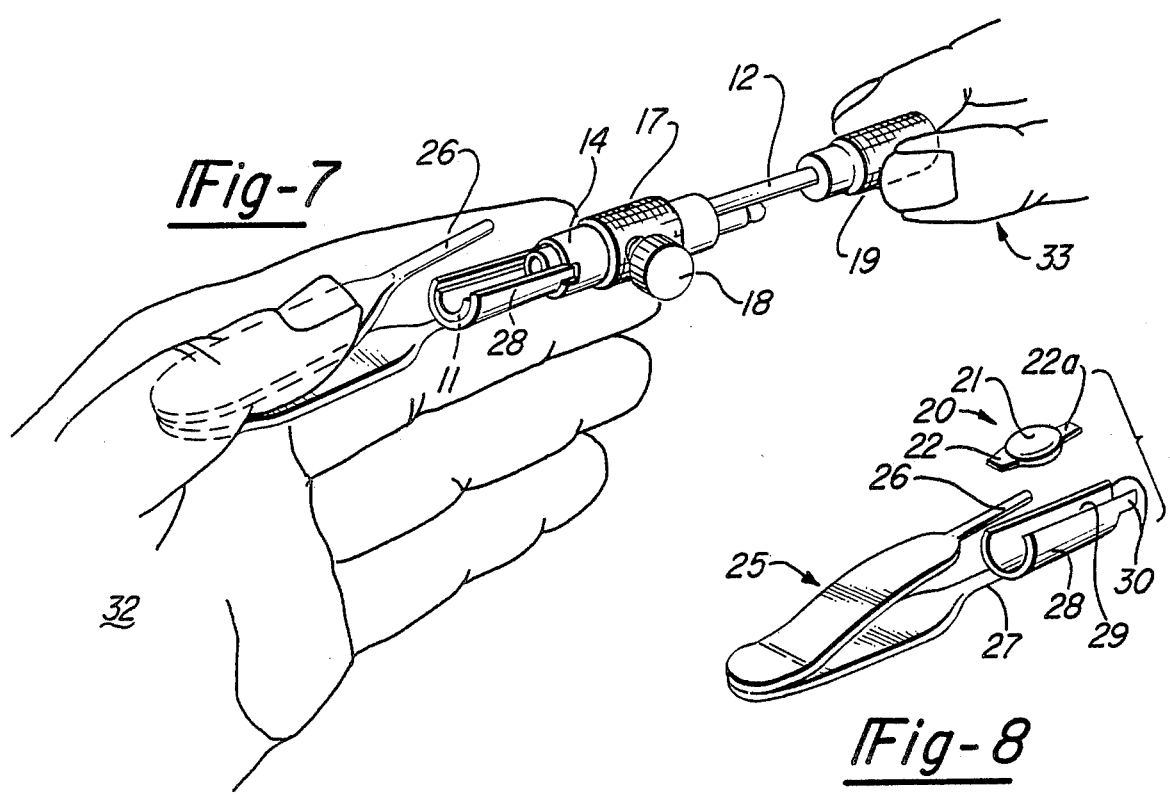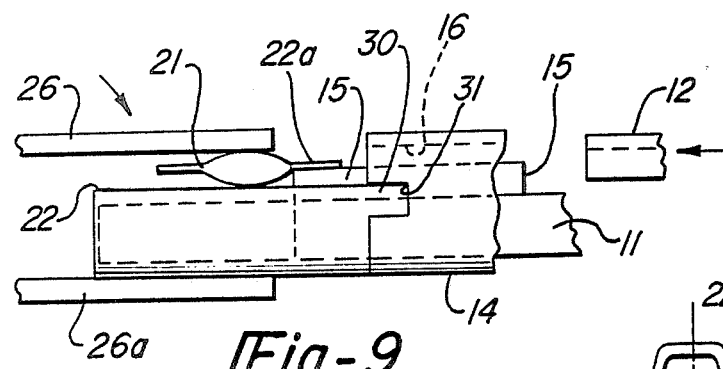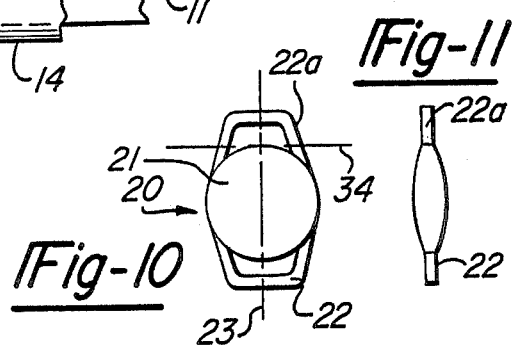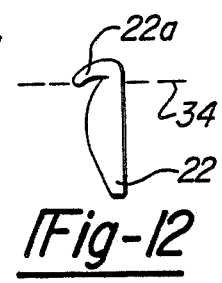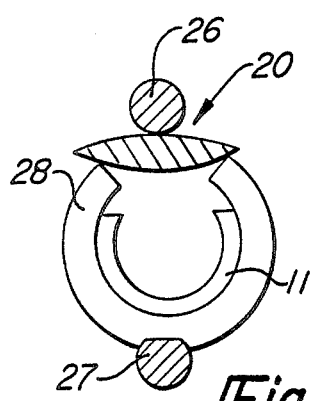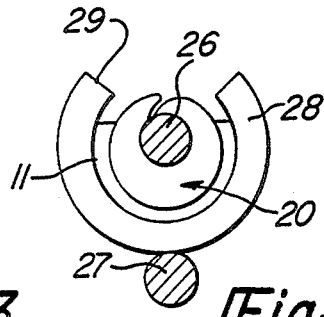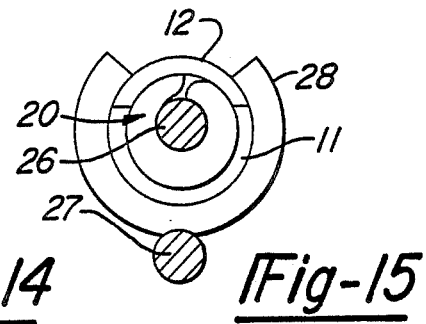

FOLDABLE INTRAOCULAR LENS INSERTER

BACKGROUND OF INVENTION

This invention relates to a surgical instrument or tool used for inserting a synthetic, intraocular lens, in folded condition, through a small incision in the limbus, into the anterior chamber of an eye.

In the surgical replacement of a defective natural lens with a synthetic lens, an incision is made in the limbus or margin of the cornea of the eye. The defective, natural lens is surgically removed through the incision, leaving the natural lens capsule within the eye. Thereafter, a synthetic lens is inserted through the incision into the anterior chamber of the eye. Then, the synthetic lens is positioned in the place of the natural lens, using a surgical instrument extending through the incision. Upon completion of the surgical procedure for positioning and holding the lens in proper position, the incision is closed with sutures and is allowed to heal.

The removal of the natural lens requires only a very small incision because the lens is emulsified with an ultrasonic probe and sucked out. However, in the past, the synthetic replacement lens, which was normally made of a rigid plastic material of a size and shape to replace the natural lens. Thus, a substantial-sized incision was required to insert the rigid lens into the anterior chamber of the eye, beneath the cornea, for subsequent positioning into the sulcus or capsule. For example, an incision on the order of roughly 12 millimeters or more was required.

More recently, a resiliently flexible or foldable synthetic plastic lens has been developed for use, instead of a rigid lens, as a replacement for the natural lens. Such foldable lens may be rolled or folded so that it can be inserted into the anterior chamber through a much smaller incision than that previously required for the rigid lens. By way of example, an incision of about 3.5-4 millimeters is adequate for insertion of the rolled or folded lens. Once the folded lens is inserted into the eye chamber, it resiliently returns to it normal, unfolded shape.

There is a substantial advantage in reducing the length of the incision in this type of eye surgery. Specifically, the smaller the incision, the less the induced astigmatism caused by the operation, the faster the wound heals, the less bleeding is encountered and there is less intraocular inflammation. With the smaller incision, the number of sutures can be reduced to the point where one or two sutures may be adequate for closing the wound. This is a substantial advantage over the previously-needed multiple sutures. Thus, there is a considerable advantage in using a foldable lens in place of the earlier, rigid synthetic lens.

However, the folding and holding of the folded lens and, particularly, the release of the folded lens from a surgical insertion tool utilized in positioning the lens has frequently caused damage to the delicate lens itself and to the tissues fo the eye. The more delicate or thinner marginal edges of the lens are especially vulnerable to damage. Attempts have been made to provide instruments or tools which can hold a folded lens during insertion and can release the lens within the anterior chamber of the eye without damaging or scratching the lens. However, presently available tools are unable to avoid damage to an inserted lens at all times. Consequently, the invention herein relates to a surgical instrument or tool which enables easy folding of a lens into the tool, which holds and permits insertion of the lens into the eye chamber, and which releases the lens without damage to the lens.

SUMMARY OF INVENTION

This invention contemplates a surgical instrument or tool for folding a lens about its thicker center portion, holding the folded lens for insertion into the anterior chamber of the eye, and releasing the folded lens within the chamber. The tool comprises an elongated tube which is split longitudinally into a lower, base section, and an upper, cover section. A guide fastened upon the base section guides the cover section for axial or longitudinal movement into position for covering the base or, alternatively, for uncovering the base. The tube can be inserted through a small surgical incision into the anterior chamber of an eye and then by manually sliding the cover section, the base is opened so that the folded lens self-releases into the anterior chamber of the eye.

The tool includes a folding device for positioning and folding the resiliently foldable lens into the tube. Such device includes a trough which receives and holds the base section of the tube while permitting longitudinal or endwise sliding of the cover section. A foldable lens may be manually positioned over the opening of the trough above the opening of the base. Then the lens may be folded and pushed into the base by means of a rod-like member. For this purpose, the trough is formed upon one leg of a forceps-like device and the rod is formed upon the opposing leg thereof.

An object of this invention is to provide a simplified, easy to operate instrument which folds the lens, holds and positions it within the eye, and releases it within the eye without damaging the lens. Thus, the instrument may be inserted through a small incision to provide the benefits of small incision surgery.

A further object of this invention is to provide an instrument which may be easily used by one person, using both his hands for operating the device without assistance or additional tools or implements. Significantly, this device positions the folded lens at the required place inside the anterior chamber of an eye and rapidly releases it for resiliently unfolding, without tearing or scratching or otherwise damaging the lens, particularly, the thinner marginal portions of the lens.

These and other objects and advantages of this invention may be further perceived upon reading the attached description, of which the attached drawings form a part.

DESCRIPTION OF DRAWINGS

FIG. 7 is a perspective view showing the inserter, with the lens folding device, held by human hands for folding a lens.

FIG. 8 is a perspective view of the folding, opthalmic forceps-type, folding device with a lens schematically positioned adjacent the device.

FIG. 9 is an enlarged fragmentary side view of the folding, forceps-type device with a lens positioned upon the support trough.

FIG. 10 is an enlarged, schematic view showing a foldable type of lens.

FIG. 11 is an end view of the lens of FIG. 10.

FIG. 12 is a view similar to FIG. 11, but showing the lens partially bent around its thickened or bulged center.

FIG. 13 is an enlarged schematic view, showing the positioning of the lens upon the folding device, preparatory to folding it into the inserter.

FIG. 14 shows the folded lens held within the inserter base.

FIG. 15 illustrates the securement of the folded lens within the tube formed by the base and the overlapping cover sections.

DETAILED DESCRIPTION

Figure 1:
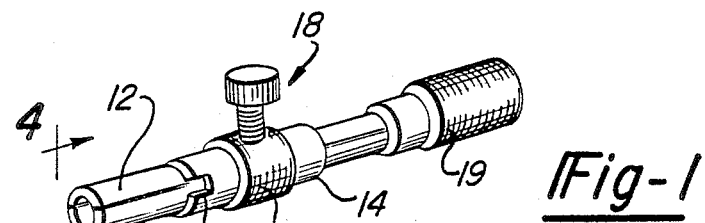
FIG. 1 is a perspective view of the lens inserter of this invention.
Figure 2:
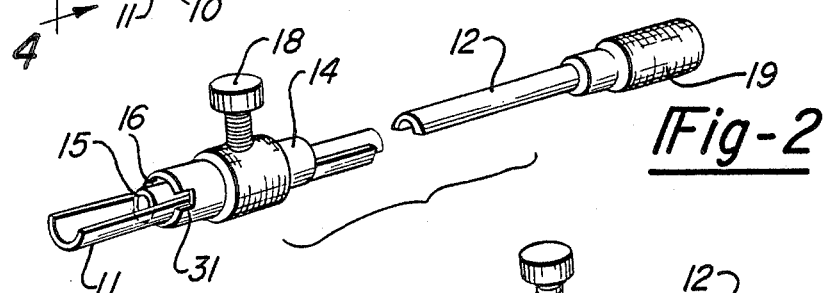
FIG. 2 is a perspective view, similar to FIG. 1, but with the cover section withdrawn.
Figure 3:
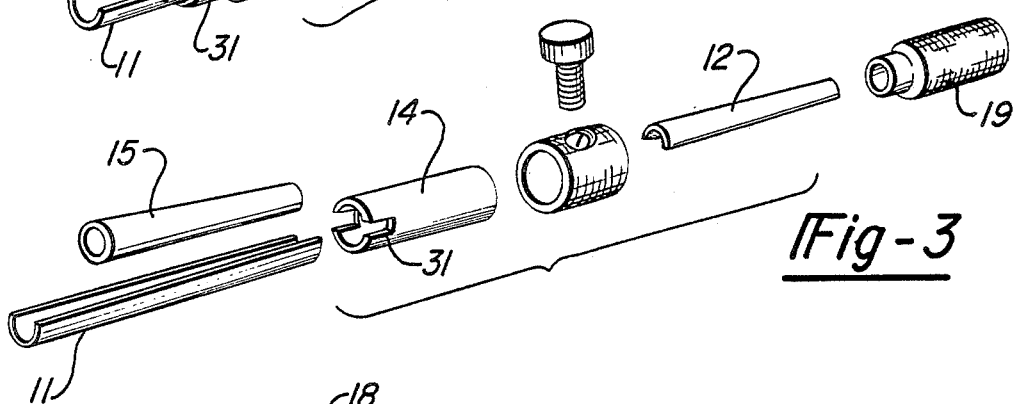
FIG. 3 is a perspective view showing the inserter parts separated.
Figure 4:
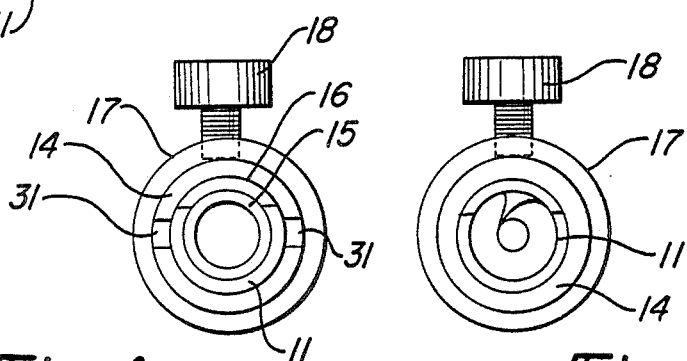
FIG. 4 is an enlarged, end view of the lens inserter, taken in the direction of arrows 4—4 of FIG. 1, without a lens.
Figure 5:
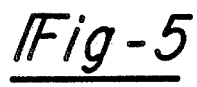
FIG. 5 is an enlarged, end view, similar to FIG. 4, but showing a lens folded within the tube.

Referring to FIGS. 1-5, the inserter comprises an elongated, insertion tube 10 (see FIG. 1). The tube is longitudinally split to form a lower, U-shaped, base section 11 and an upper, U-shaped cover section 12. The two sections are normally overlapped to make up the complete tube. However, the cover section is manually slideable longitudinally or axially relative to the base section so that the base section may be either uncovered or covered by the overlapping cover section.

A guide is provided to position and guide the sliding movement of the cover section. The guide is formed of a tubular sleeve 14 which surrounds the base section and is secured to the base section, such as by soldering or the like. A plug, in the form of a cylindrical tube 15, is fastened within the base section and is surrounded by the sleeve. The plug is preferably of sufficient length so as to extend outwardly of the sleeve at its opposite ends.

An arcuate space or slot 16 (see FIGS. 2 and 4) is provided between the exterior surface of the plug 15 and the interior wall surface of the sleeve 14. This arcuate space or slot 16 forms a guide through which the cover section 12 is slideably moved.

A knurled grip or handle 17 is mounted upon the sleeve 15 and is locked in position by a knurled head set screw 18 which is threadedly engaged within a corresponding opening in the handle sleeve. This handle sleeve and the screw form a convenient handle or grip for manual manipulation of the device. Loosening the set screw permits the user to rotate or slide the handle sleeve and screw into a position most convenient for his use. In addition, a knurled grip or handle 19 is secured on the end of the cover section 12.

The inserter is used for folding a soft, resiliently foldable, plastic lens 20 (see FIGS. 10-12) and then inserting the folded lens into the anterior chamber of the eye. One available lens for this purpose is made of a silicone plastic material which can be resiliently folded in half and which, upon release, will resiliently return to its original unfolded position and shape. The lens 20 is provided with a centrally bulged lens portion 21 and opposite edge fins 22 and 22a. Although the size of the lens may vary, a typical size would be roughly in the range of 6 mm in transverse direction and 11.5 mm along the lengthwise or center-line 23 direction.

An object is to fold or roll the lens around its thicker center, i.e. along its center line 23, without crushing the lens, to hold it in its folded position and finally to release it for self-unfolding, all without damaging the fragile lens. For this purpose, a folding device, used with the inserter, will fold and hold the folded lens within the base section 11 of the tube until the cover section 12 is placed into overlapping relationship with the base for confining the lens within the tube. The folding device may be made of an ophthalmic forceps 25, with upper and lower elongated, rod-like leg extensions 26 and 27. A U-shaped arcuate trough 28 is mounted upon the lower leg 27 (see. FIGS. 8-9). The trough is preferably made of a resilient metal sheet and is of an arcuate, cross-sectional shape. The arc of the trough is greater than the arc of the base. For example, the arc of trough may be roughly 320°, as compared with the arc of base 11 being about 220°. This leaves a narrow, slot opening 29 on the trough which is roughly 40° in angle.

A pair of lugs 30 are integrally formed of the free end of the trough. These lugs snugly slide into slots or sockets 31 formed in the adjacent end of the sleeve 14 to temporarily connect the sleeve and trough (see FIG. 7).

In operation, the base section 11 is placed within the trough 28 where it is held by friction and the lugs 30 frictionally engaged within the sockets 31. The forceps 25 and the entire inserter may be positioned upon one hand 32 or upon a table. The cover section 12 is slid outwardly by the other hand 33 as shown schematically in FIG. 7. Then, a lens 20 is manually positioned upon the trough, spanning the slot 29, as illustrated in FIGS. 9 and 13. Preferably, one fin 22a is arranged over the upper surface of the end of the plug 15 (see FIG. 9). The rod-like leg 26 is moved downwardly through the slot 29 and into the trough 28 and base section 11 by pressure from the user's thumb. Meanwhile, the instrument is steadied by the sleeve handle 17 and the set screw 18 being arranged upon and supported by the user's fingers. For the purpose, the sleeve handle may be turned so that the set screw 18 extends sidewise relative to the upper opening of the base section 12.

When the leg 26 is moved inwardly of the trough and base section, as shown in FIG. 14, the lens is curled or folded around its longitudinal center line 23, that is, around its thicker central portion. Simultaneously, because leg 26 is shorter than the length of the trough and does not engage the fin 22a, and fin 22a is temporarily held up by its contact with the plug, that fin folds around a transverse fold line 34 located approximately where it joins the bulged center portion 21 (see FIG. 10). The folded fin (shown in FIG. 12) bends around the folded lens central portion.

Next, the user grasps the cover section grip 19 and slides the cover section into overlapping relationship with the base section, as shown in FIG. 15, to confine the doubly-folded lens within the end of the tube. As can be seen in the drawing, the lens is curled around the rod-like leg so that it does not crush.

The folding device is pulled endwise away from the inserter to withdraw the leg 26 from the folded or rolled lens and to remove the trough from the end of the tube. At this point, the inserter is ready for use for inserting the lens into the anterior chamber of the eye for implanting the lens.

Figure 6:
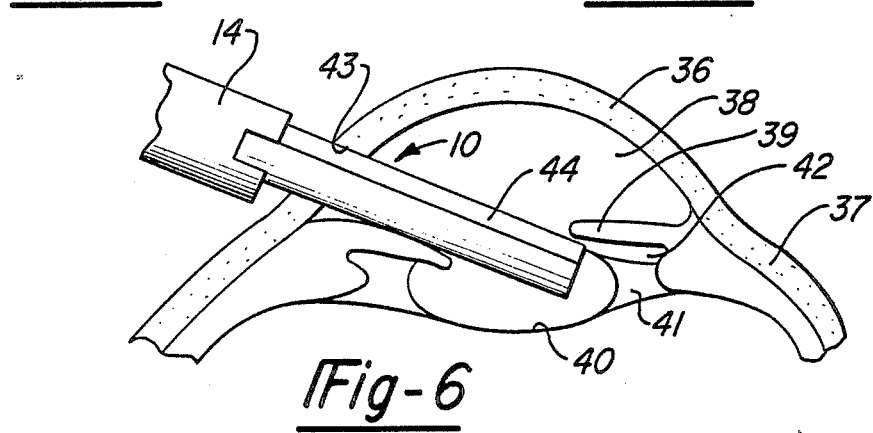
FIG. 6 is an enlarged, schematic, cross-sectional type view of a portion of a human eye, with a portion of the inserter shown in position within the eye for release of the folded lens contained within the inserter.

The surgical procedure for using the inserter is schematically illustrated in FIG. 6 which shows a portion of a human eye. The drawing shows the cornea 36, sclera 37, anterior chamber 38 and iris 39. Below the iris is the capsule 40 which originally contained the natural lens that had been surgically removed. The capsule is supported by a suspensory ligament 41 which provides a posterior chamber 42 beneath the iris.

At the outset of the operation, the surgeon makes a small incision 43 (e.g. approximately 3.5–4 mm) in the limbus or margin of the cornea. The natural lens is removed through that incision after being disintegrated.

As shown in FIG. 6, the inner end portion 44 of the inserter tube 10 is inserted through the small incision into the limbus. The surgeon properly positions the tube, as illustrated, by way of example, in FIG. 6, for release of the lens. At that point, the cover section is pulled outwardly to uncover the base section and expose the lens. The lens, being resilient, will resiliently unfold and pop out of the base section. Then, the inner end portion of the tube is withdrawn from the chamber.

After the lens is positioned within the chamber, it resiliently returns to its original shape. Meanwhile, the surgeon, by inserting appropriate instruments through the small incision, positions a lens within the capsule or ciliary sulcus to complete the implanting of the lens.

Significantly, the folded or rolled lens is not pushed or manipulated in order to release it from the tube. It simply pops out as it unfolds. Thus, damage to the lens is avoided. The thin margins of the lens, being springier than the thicker center portion of the lens easily yield while the upper section of the tube is withdrawn to avoid damaging the folded lens.

Having fully described an operative embodiment of this invention, we now claim:

1. A foldable intraocular lens inserter comprising:
    an elongated tube split longitudinally to form a U-shaped in cross-section elongated base and an overlapping U-shaped elongated in cross-section cover;
    said tube having an inner end portion and an outer end portion;
    the cover being manually, axially slidable relative to the base for overlapping the base to form the complete tube therewith and for uncovering the base inner end portion;
    guide means fixedly secured to the base outer end portion for guiding the cover for sliding along the tube axis towards and away from the tube inner end portion in axial alignment with the base and for holding the cover in overlapping position upon the base;
    whereby a resiliently foldable lens may be positioned upon and folded into the base when the cover is manually slid axially in an outwardly direction relative to the tube, and may be enclosed in folded condition, within the inner end portion of the tube when the cover is slid into position for overlapping the base, and the tube may be inserted into the anterior chamber of an eye through a small incision and, thereafter, the cover may be slid outwardly for uncovering the base so as to release the folded lens within the eye chamber for resiliently unfolding therein.

2. A foldable intraocular inserter as defined in claim 1, and including:
    said guide means comprising a tubular sleeve surrounding and secured to the outer end portion of the base, and a cylindrical plug secured within the base general area that is encircled by the sleeve to form an arcuate space between the interior wall of the sleeve and the exterior wall of the plug, into which space the cover is inserted for thereby guiding and positioning the cover relative to the base.

3. A foldable intraocular lens inserter as defined in claim 2, and with the outer end portion of the cover having an enlarged manual grip portion for manually holding the outer end of the cover and for moving it axially relative to the base.

4. An apparatus for inserting a foldable intraocular lens, comprising:
    an elongated tube split longitudinally to form a U-shaped in cross-section elongated base and an overlapping U-shaped elongated in cross-section cover;
    said tube having an inner end portion and an outer end portion;
    the cover being manually, axially slidable relative to the base for overlapping the base to form the complete tube therewith and for uncovering the base inner end portion;
    guide means fixed secured to the base outer end portion for guiding the cover for sliding along the tube axis towards and away from the tube inner end portion in axial alignment with the base and for holding the cover in overlapping position upon the base;
    means for folding the lens within the uncovered base and holding the folded lens within the base until the base is overlapped by the cover;
    said means comprising a support member removably supporting the base inner end portion and an elongated rod positioned over the support member and arranged generally parallel to the base axis and being manually movable towards the base for folding a lens around its thicker center area and for holding the lens in folded position until the cover is slid into position overlapping the base for encircling the lens within the tube inner end portion;
    whereby the lens may be positioned upon and folded into the base when the cover is manually slid axially in an outwardly direction relative to the tube, and may be enclosed in folded condition, within the inner end portion of the tube when the cover is slid into position for overlapping the base, and the tube may be inserted into the anterior chamber of an eye through a small incision and, thereafter, the cover may be slid outwardly for uncovering the base so as to release the folded lens within the eye chamber for resiliently unfolding therein.

5. An apparatus as defined in claim 4, and including:
    said support member being formed of a generally U-shaped in cross-section trough of a length which is roughly the same as the inner end portion of the tube, such trough being of a size to snugly receive and hold the inner end portion of the base, and having upper, generally parallel edges, upon which the unfolded lens may be supported above the base so that the lens may be folded into the base by the rod and the rod may be removed endwise from the base thereafter.

6. An apparatus as defined in claim 5, and including said trough having a cross-sectional arc which is considerably greater than the cross-sectional arc of the base, so that the trough encloses the base and extends, in cross-section beyond the edges forming the U-shaped base, so that the lens, before folding, is held above the base, and the portions of the trough extending beyond the base function to guide and confine the folded lens under the cover as it is slid into overlapping position relative to the base.

7. An apparatus as defined in claim 6, and wherein the lens includes a bulged center portion and integral, oppositely extending, longitudinally directed thin fins,
and said guide means including a portion arranged to temporarily support one of the fins of the lens while the rest of the lens is folded along its longitudinal axes to thereby fold the supported fin, around a transverse fold axis, into the base.

8. A surgical apparatus for folding and inserting an intraocular lens within the anterior chamber of an eye, comprising:
an elongated tube formed of two overlapping, elongated U-shaped sections, one section forming a base and the other section forming a longitudinally slidable cover for the base;
guide means secured to the base for guiding and holding the cover for axial sliding movement upon the base;
means for supporting a foldable lens having a bulged center portion and thinner marginal edge portions, adjacent the open mount of the U-shaped base adjacent an end thereof;
an elongated rod member arranged for movement, normal to its axial direction, into the base for engaging and folding the lens about its bulged middle portion into the base and for holding the folded lens within the base until the cover is axially slid to cover the base so that the rod may be withdrawn therefrom;
whereby the tube may be inserted within the anterior chamber of the eye through a small surgical incision and the cover may be axially moved relative to the base, for uncovering the base and thereby permitting the lens to resiliently self-eject from the base and unfold within the chamber.

9. A surgical apparatus as set forth in claim 8, including said means for supporting the lens comprising a generally circular in cross-section tubular trough having a slot along its length, with the edges defining the slot supporting the lens adjacent the U-shaped base and the rod formed to move through the slot and into the base for folding the lens.

10. An apparatus for inserting a foldable intraocular lens, comprising:
a lens inserter including an elongated tube split longitudinally to form a U-shaped in cross-section elongated base and an overlapping U-shaped elongated in cross-section cover;
said tube having an inner end portion and an outer end portion;
the cover being manually, axially slidable relative to the base for overlapping the base to form the complete tube therewith and for uncovering the base inner end portion;
guide means fixedly secured to the base outer end portion for guiding the cover for sliding along the tube axis towards and away from the tube inner end portion in axial alignment with the base and for holding the cover in overlapping position upon the base;
means for folding the lens within the uncovered base and holding the folded lens within the base until the base is overlapped by the cover;
said means including a support member removably supporting the base inner end portion and an elongated rod positioned over the support member and arranged generally parallel to the base axis and being manually movable towards the base for folding a lens around its thicker center area and for holding the lens in folded position until the cover is slid into position overlapping the base for encircling the lens within the tube inner end portion;
said support member being formed of a generally U-shaped in cross-section trough of a length which is roughly the same as the inner end portion of the tube, such trough being of a size to snugly receive and hold the inner end portion of the base, and having upper, generally parallel edges, upon which the unfolded lens may be supported above the base so that the lens may be folded into the base by the rod and the rod may be removed endwise from the base thereafter;
said trough having a cross-sectional arc which is considerably greater than the cross-sectional arc of the base, so that the trough encloses the base and extends, in cross-section beyond the edges forming the U-shaped base, so that the lens, before folding, is held above the base, and the portions of the trough extending beyond the base function to guide and confine the folded lens under the cover as it is slid into overlapping position relative to the base;
said trough being mounted upon one of the two legs of an ophthalmic-type forceps and the rod forming a portion of the opposite leg of said forceps;
whereby the forceps and the lens inserter, with the base held within the trough and supporting the unfolded lens, may be held in one hand and the lens may be positioned upon and folded about its thicker, central portion, into the base by manually squeezing the forceps while the cover is manually slid axially in an outwardly direction, relative to the tube, and may be enclosed in folded condition, within the inner end portion of the tube when the cover is slid into position for overlapping the base, and the tube may be inserted into the anterior chamber of an eye through a small incision and, thereafter, the cover may be slid outwardly for uncovering the base so as to release the folded lens within the eye chamber for resiliently unfolding therein with the folding and positioning of the lens within the inserter accomplished rapidly by one person without additional tools.

* * * * *